(12) United States Patent
Sugimura

(10) Patent No.: US 8,586,706 B2
(45) Date of Patent: *Nov. 19, 2013

(54) PEPTIDE VACCINE USING MIMIC MOLECULES OF AMYLOID β PEPTIDE

(75) Inventor: Kazuhisa Sugimura, Kagoshima (JP)

(73) Assignee: Kagoshima University, Kagoshima-Shi, Kagoshima (JP)

( * ) Notice: Subject to any disclaimer, the term of this patent is extended or adjusted under 35 U.S.C. 154(b) by 299 days.

This patent is subject to a terminal disclaimer.

(21) Appl. No.: 12/739,651

(22) PCT Filed: Oct. 22, 2008

(86) PCT No.: PCT/JP2008/069586
§ 371 (c)(1),
(2), (4) Date: Apr. 23, 2010

(87) PCT Pub. No.: WO2009/054537
PCT Pub. Date: Apr. 30, 2009

(65) Prior Publication Data
US 2010/0331262 A1    Dec. 30, 2010

(30) Foreign Application Priority Data
Oct. 25, 2007  (JP) .................................. 2007-277638

(51) Int. Cl.
C07K 7/00    (2006.01)
A61K 38/00   (2006.01)
A61K 38/04   (2006.01)
A61P 25/00   (2006.01)

(52) U.S. Cl.
USPC ........................ 530/329; 514/17.7; 514/21.7

(58) Field of Classification Search
None
See application file for complete search history.

(56) References Cited

U.S. PATENT DOCUMENTS

| 2004/0034043 A1 | 2/2004 | Katzhendler et al. |
| 2006/0111301 A1 | 5/2006 | Mattner |
| 2008/0051690 A1 | 2/2008 | Mattner et al. |
| 2009/0088386 A1 | 4/2009 | Sugimura |

FOREIGN PATENT DOCUMENTS

| EP | 1741783 A1 | 1/2007 |
| JP | 2004-520261 T | 7/2004 |
| JP | 2006-515876 A | 6/2006 |
| WO | 2004/062556 A2 | 7/2004 |
| WO | 2005/033311 A2 | 4/2005 |
| WO | 2005/105998 A1 | 11/2005 |
| WO | 2006/005706 A2 | 1/2006 |
| WO | 2006/005707 A2 | 1/2006 |
| WO | WO 2006/005707 * | 1/2006 |
| WO | WO 2007/126111 A1 | 8/2007 |

OTHER PUBLICATIONS

Davies et al., 2009, Mechanism-based treatments for Alzheimer's disease, Dialogues Clin. Neurosci., 11(2): 159-169.*
Wang et al., 2006, Clearance of amyloid-beta in Alzheimer's disease: progress, problems, and perspectives, Drug Discovery Today, 11: 931-938.*
Search Report issued Sep. 13, 2011, in European Patent Application No. 08841003.0.
Tanaka et al., "A mimotope peptide of ABeta42 fibril-specific antibodies with fibrilation inhibitory activity induces anti-ABeta42 conformer antibody response by a displayed form on an M13 phage in mice," Journal of Neuroimmunology (2011), vol. 236, pp. 27-38.

* cited by examiner

*Primary Examiner* — Amber D Steele
(74) *Attorney, Agent, or Firm* — Birch, Stewart, Kolasch & Birch, LLP

(57) ABSTRACT

This invention is intended to discover a peptide that induces production of an antibody specific for an abnormal amyloid β peptide from mimic peptides of the amyloid β peptide and to utilize the same as a vaccine or immunogen. This invention relates to a pharmaceutical composition containing a peptide consisting of 8 to 30 amino acid residues, wherein the peptide comprises at least one of an amino acid sequence represented by formula (I): Tyr-Gly-Thr-Lys-Pro-Trp-Met (SEQ ID NO: 28) (I), and an amino acid sequence represented by formula (II): Leu-Asp-Ile-Phe-Ala-Pro-Ile (SEQ ID NO: 29) (II); or a conjugate of such peptide and a carrier.

5 Claims, 10 Drawing Sheets

Fig. 5

| Name of phage clone | Name of template antibody | Amino acid sequence of peptide |
|---|---|---|
| pepB6-L1 | B6 | G M L D I F A P I R H V |
| pepB6-L10 | B6 | T S P I L D V L T P P R |
| | | |
| 12 mer* | | |
| pepD1-L1, L8, L15 | D1 | R V D I L N Y L S P P I |
| pepD1-L5, L9 | D1 | G S P F L D L L A P A A |
| pepD1-L6 | D1 | S S I I D I L L P P I Y |
| pepD1-L7 | D1 | S I L D I L S P R L A E |
| pepD1-L13 | D1 | G N T L L D T L V P L I |
| pepD1-L20 | D1 | N P L D F Y A P S I L P |
| pepD1-L2 | D1 | S P L F A M L A P A V D |
| | | |
| pepB6-C2, C5, C6, C7, C8, C9, C10, C15 | B6 | C Y G T K P W M C |
| | | |
| C7C* | | |
| pepB7-C15 | B7 | C Y G T K P W M C |
| pepD1-C2, C13 | D1 | C Y G T E P W M C |
| pepD1-C18 | D1 | C F G H E P W M C |
| pepD1-C3 | D1 | C Q G H L P W M C |
| pepD1-C11 | D1 | C F G H K P W M C |
| pepD1-C5, C7, C20 | D1 | C Y G T K P W M C |
| pepD1-C8 | D1 | C F G R L P W M C |
| pepD1-C10 | D1 | C F G S L P W M C |

Fig. 6

| Name of binding sequence | Amino acid sequence |
|---|---|
| B6-L1 | GMLDIFAPIRHV |
| B7-C15 | CYGTKPWMCG |
| B7-S15 | SYGTKPWMSG |
| TAT | YGRKKRRQRRR |
| | |
| TAT-B6-L1 | biotin-YGRKKRRQRRRGMLDIFAPIRHV |
| B6-L1-TAT | biotin-GMLDIFAPIRHVYGRKKRRQRRR |
| TAT-B7-C15 | biotin-YGRKKRRQRRRCYGTKPWMCG |
| TAT-B7-S15 | biotin-YGRKKRRQRRRSYGTKPWMSG |

Anti-Aβ antibody/HRP labeled-antibody mouse antibody

PEPTIDE VACCINE USING MIMIC MOLECULES OF AMYLOID β PEPTIDE

TECHNICAL FIELD

The present invention relates to a peptide vaccine that is useful as a preventive and/or therapeutic agent for Alzheimer's disease.

BACKGROUND ART

With an increase in the population of senior citizens, development of pharmaceutical products that are effective for treatment of senile dementia has been strongly awaited in recent years. A typical senile dementia disease; i.e., Alzheimer's disease, is a neurodegenerative disease characterized by brain shrinkage, senile plaque deposition, and neurofibrillary changes. The configuration of amyloid β peptide is changed, and insoluble molecules resulting from fibrillogenesis caused by such change are deposited in nerve cells. Nerve cell death is induced by toxicity of the insoluble molecules, and Alzheimer's disease is then developed.

Amyloid β peptide (Aβ) is a degradation product resulting from a neuron amyloid precursor protein via cleavage with, for example, β secretase, and two types thereof; i.e., Aβ1-40 and Aβ1-42, are generated. Aβ1-42 more easily aggregates, and Aβ1-42 is reported to be more often correlated with diseases and neurotoxicity.

If the changes in amyloid β peptide configuration and the fibrillogenesis caused by the changes could be inhibited, development of Alzheimer's disease could be suppressed.

WO 2005/105998 discloses that a single-stranded antibody that has activity of binding specifically to Aβ1-42 and inhibiting the fibrillogenesis is useful as a preventive and/or therapeutic agent for Alzheimer's disease.

Since antibodies are high-molecular-weight proteins, disadvantageously, antibodies are expensive, the processes of production and purification thereof are laborious, and the stabilities of antibodies are insufficient.

The development of vaccines is a means for inducing such immune response in humans, and the most critical issue of concern is the substance to be used as an immunogen.

At present, many reports have been made regarding the use of peptides as vaccines for prevention and treatment of Alzheimer's disease; for example, use of part of a normal amyloid β amino acid sequence as an antigen (e.g., WO 2006/121656; G. G Kinney et al., A Novel anti-amyloid beta active vaccine approach for the treatment of Alzheimer's and related disorders, Neuro-degenerative Diseases, 4: supplement 1, p. 251, 2007) and use of a newly developed peptide sequence referred to as an amyloid β mimotope as an antigen (JP Patent Publication (kohyo) No. 2006-515876 A; M. Mandler et al., The AFFiR is mimotope vaccine: A novel approach for the treatment of AD, Neuro-degenerative Diseases, 4: supplement 1, p. 250, 2007).

DISCLOSURE OF THE INVENTION

The goal of the present invention relates to the discovery of a peptide that induces production of an antibody specific for an abnormal amyloid β peptide from a mimic peptide of an amyloid β peptide and the utilization of the same as a vaccine or immunogen.

The present invention is summarized as follows.

(1) A pharmaceutical composition containing a peptide consisting of 8 to 30 amino acid residues, wherein the peptide comprises at least one of an amino acid sequence represented by formula (I):

Tyr-Gly-Thr-Lys-Pro-Trp-Met (SEQ ID NO: 28)(I), and an amino acid sequence represented by formula (II):

Leu-Asp-Ile-Phe-Ala-Pro-Ile (SEQ ID NO: 29)(II); or a conjugate of such peptide and a carrier.

(2) The pharmaceutical composition according to (1), which contains a peptide consisting of 9 to 30 amino acid residues, wherein the peptide comprises at least one of an amino acid sequence represented by formula (Ia):

```
                                    (SEQ ID NO: 35)
    Cys-Tyr-Gly-Thr-Lys-Pro-Trp-Met-Cys (Ia)
```

(wherein two cysteine residues may be crosslinked), an amino acid sequence represented by formula (Ib):

Ser-Tyr-Gly-Thr-Lys-Pro-Trp-Met-Ser-Gly (SEQ ID NO: 23) (Ib), and an amino acid sequence represented by formula (IIa):

Gly-Met-Leu-Asp-Ile-Phe-Ala-Pro-Ile-Arg-His-Val (SEQ ID NO: 9)(IIa); or a conjugate of such peptide and a carrier.

(3) The pharmaceutical composition according to (1) or (2), wherein the peptide consists of 20 to 30 amino acid residues containing the aforementioned amino acid sequence or sequences and a TAT sequence represented by formula:

```
                                    (SEQ ID NO: 35)
    Tyr-Gly-Arg-Lys-Lys-Arg-Arg-Gln-Arg-Arg-Arg.
```

(4) The pharmaceutical composition according to any one of (1) to (3), which further contains an adjuvant.

(5) The pharmaceutical composition according to any one of (1) to (4), which is an inhibitor of amyloid β fibrillogenesis.

(6) The pharmaceutical composition according to any one of (1) to (5), which is a preventive and/or therapeutic agent for Alzheimer's disease.

(7) An immunogen containing a peptide consisting of 8 to 30 amino acid residues, wherein the peptide comprises at least one of an amino acid sequence represented by formula (I):

Tyr-Gly-Thr-Lys-Pro-Trp-Met (SEQ ID NO: 28) (I), and an amino acid sequence represented by formula (II):

Leu-Asp-Ile-Phe-Ala-Pro-Ile (SEQ ID NO: 29) (II); or a conjugate of such peptide and a carrier.

(8) The immunogen according to (7), which contains a peptide consisting of 9 to 30 amino acid residues, wherein the peptide comprises at least one of an amino acid sequence represented by formula (Ia):

```
                                    (SEQ ID NO: 35)
    Cys-Tyr-Gly-Thr-Lys-Pro-Trp-Met-Cys (Ia)
```

(wherein two cysteine residues may be crosslinked), an amino acid sequence represented by formula (Ib):

Ser-Tyr-Gly-Thr-Lys-Pro-Trp-Met-Ser-Gly (SEQ ID NO: 23) (Ib), and an amino acid sequence represented by formula (IIa):

Gly-Met-Leu-Asp-Ile-Phe-Ala-Pro-Ile-Arg-His-Val (SEQ ID NO: 9) (IIa); or a conjugate of such peptide and a carrier.

(9) The immunogen according to (7) or (8), wherein the peptide consists of 20 to 30 amino acid residues containing the aforementioned amino acid sequence or sequences and a TAT sequence represented by formula:

Tyr-Gly-Arg-Lys-Lys-Arg-Arg-Gln-Arg-Arg-Arg. (SEQ ID NO: 30)

The peptide used in the present invention consists of 8 to 30 amino acid residues, wherein the peptide comprises at least one of an amino acid sequence represented by formula (I):
Tyr-Gly-Thr-Lys-Pro-Trp-Met (SEQ ID NO: 28) (I), and an amino acid sequence represented by formula (II):

Leu-Asp-Ile-Phe-Ala-Pro-Ile. (II) (SEQ ID NO: 29)

The peptide used in the present invention may comprise the amino acid sequence represented by formula (I) and the amino acid sequence represented by formula (II).

An example of the peptide used in the present invention is a peptide consisting of 9 to 30 amino acid residues, wherein the peptide comprises at least one of an amino acid sequence represented by formula (Ia):

Cys-Tyr-Gly-Thr-Lys-Pro-Trp-Met-Cys (Ia) (SEQ ID NO: 35)

(wherein two cysteine residues may be crosslinked), an amino acid sequence represented by formula (Ib):
Ser-Tyr-Gly-Thr-Lys-Pro-Trp-Met-Ser-Gly (SEQ ID NO: 23) (Ib), and an amino acid sequence represented by formula (IIa):

Gly-Met-Leu-Asp-Ile-Phe-Ala-Pro-Ile-Arg-His-Val (IIa).

In the peptide used in the present invention, amino acid sequences other than the amino acid sequence represented by formula (I) or (II) are not particularly limited, provided that peptides consisting of such amino sequences are pharmaceutically acceptable. Examples thereof include a TAT sequence represented by formula: Tyr-Gly-Arg-Lys-Lys-Arg-Arg-Gln-Arg-Arg-Arg (SEQ ID NO: 30), an amino acid sequence that enhances peptide solubility (e.g., a sequence comprising several basic amino acids such as arginine or lysine), and an amino acid sequence that enhances cell membrane permeability (e.g., a partial sequence of leptin, IGF-1, IGF-2, insulin, or transferrin) (1: W. M. Pardridge, Vector-mediated drug delivery to the brain, Advanced Drug Delivery Reviews, 36: 299-321, 1999; and 2: W. M. Pardridge, Drug and gene targeting to the brain with molecular trojan horses, Nature Reviews' Drug discovery, 1: 131-139, 2002).

The peptide used in the present invention can be chemically synthesized via conventional techniques. For examples, the peptide can be synthesized with the use of an automated peptide synthesizer. The method described in R.B. Merifield, Advance in Enzymology 32:221-296, 1969 can be employed for a basic synthesis process. In this technique, an amino acid at the carboxyl terminus is covalently bound to a resin carrier, a process of removal of a protecting group for an α-amino group followed by condensation of the protected amino acid is repeated so as to extend the peptide chain toward the amino terminus, and peptide resin having a target amino acid sequence is thus obtained.

Condensation of amino acids, removal of protecting groups for α-amino groups, and the like are carried out under substantially the same conditions with the use of Boc and Fmoc without purifying intermediates. Thus, advanced skills would not be necessary for synthesis, in general. Further, this method can be rapidly completed and this method is very convenient for synthesis of various types of peptides. The thus-obtained protected peptide resin is allowed to react with, for example, anhydrous hydrogen fluoride, trifluoromethanesulfonic acid, or trifluoroacetic acid in the presence of various additives. Thus, detachment of a peptide from resin and removal of all protecting groups can be carried out in a single step.

With the use of a resin for synthesizing a peptide having a carboxyl terminal carboxylic acid as a resin carrier, a peptide having a carboxyl group at the carboxyl terminus can be obtained. With the use of a resin for synthesizing a peptide having a carboxyl terminal amide, a peptide having an amidated carboxyl terminal carboxylic acid can be obtained.

The resulting crude peptide can be purified via a known means for peptide purification. Examples thereof include: column chromatography techniques based on various principles, such as gel filtration chromatography, ion-exchange chromatography using cation-exchange resin or anion-exchange resin, hydrophobic chromatography, and partition-adsorption chromatography; and high-performance liquid chromatography.

The peptide used in the present invention may be crosslinked between cysteine residues. Cysteine residues may be crosslinked via direct disulfide crosslinking. Alternatively, disulfide crosslinking may be carried out using a disulfide compound as a spacer. Disulfide crosslinkage can be formed by, for example, oxidizing a dilute aqueous solution of peptides with $K_3[Fe(CN)_6]$ or oxidizing the same with acidic iodine.

The peptide used in the present invention can be obtained in the form of various salts. Examples of such salts include: salts with inorganic acids or organic acids, such as formic acid, acetic acid, tartaric acid, or citric acid; and salts with inorganic bases, such as sodium or ammonia, or organic bases, such as triethylamine, ethylamine, or methylamine.

The peptide used in the present invention (hereafter referred to as a "mimic peptide") is preferably bound to a carrier, such as a protein, polysaccharide, or glycoprotein, in order to enhance immunogenicity. A molecule having immunogenicity in humans can be used as a carrier. Preferably, a molecule is not toxic to humans and it would not cause side effects to humans even if an immune response is induced by such molecule. Examples of preferable carriers include bacteria- or virus-derived molecules, such as tetanus toxoid, diphtheria toxoid, pertussis vaccine, or diphtheria pertussis tetanus vaccine, BCG vaccine, keyhole limpet hemocyanin, an outer membrane protein complex (OMPC) of *Neisseria meningitidis*, dextran, mannose, and mannan. When the composition of the present invention is orally administered, the mimic peptide may be bound to a protein component of a food product. Alternatively, a food protein containing such peptide sequence is prepared via genetic modification, and the resultant may be eaten as food as a means of oral immunization.

A carrier may be bound to any of the amino terminus, carboxyl terminus, or amino acid residue in the sequence of the mimic peptide used in the present invention. Also, a plurality of mimic peptides may be bound to or polymerized with a molecule of carrier.

Methods of binding a mimic peptide to a carrier are not particularly limited. Examples include: 1) a mimic peptide is directly bound to a carrier via a covalent bond; 2) a mimic peptide is crosslinked with a carrier with the aid of a crosslinker (e.g., the glutaraldehyde method, the 1-ethyl-3-(3-dimethylaminopropyl)carbodiimide method, the maleimidobenzoyl-N-hydroxysuccinimide ester method, the bisdiazotized benzidine method, or the N-succinimidyl-3-(2-pyridyldithio)propionate method); 3) a method utilizing binding of biotin and streptavidin or avidin; and 4) a mimic peptide is arranged to fuse in series with a carrier as DNA sequences to prepare a gene recombinant. A mimic peptide may be biotinylated at the amino terminus, carboxyl terminus, or amino acid residue in the sequence. An amino group of a peptide can be biotinylated via the conventional HOBt-DCC or HBTu-HOBt method in which an amino acid derivative is condensed on resin.

A mimic peptide or a conjugate of a mimic peptide and a carrier is preferably administered in combination with an adjuvant. Known adjuvants for human vaccines, such as Freund's complete adjuvant, Freund's incomplete adjuvant, aluminum hydroxide adjuvant, or pertussis adjuvant, can be used.

The pharmaceutical composition of the present invention has effects of inducing production of an antibody specific for abnormal amyloid β peptide, and it can be used for prevention and/or treatment of Alzheimer's disease as a vaccine.

The immunogen of the present invention has effects of inducing production of an antibody specific for abnormal amyloid β peptide, and it can be used for production of an antibody specific for abnormal amyloid β peptide.

The composition containing a mimic peptide or a conjugate of such peptide and a carrier used in the present invention (hereafter it is referred to as a "vaccine component") can be orally or parenterally (preferably hypodermically, intracutaneously, or nasally) administered in that state or in the form of a pharmaceutical composition comprising a known pharmaceutically acceptable carrier, an excipient, or the like.

Specific examples of dosage forms for oral administration include tablets, pills, capsules, granules, fine grains, powders, syrup, emulsions, and suspensions. Such dosage forms are prepared in accordance with known techniques and the dosage forms include carriers or excipients that are commonly used in the field of drug preparation. Examples of carriers and excipients for tablets include lactose, maltose, sucrose, starch, and magnesium stearate. When a mimic peptide is bound to a protein component of a food product as described above or when a food protein containing the peptide sequence is prepared via gene modification, the mimic peptide can be ingested as food.

Examples of dosage forms for parenteral administration include injection preparations, poultices, suppositories, nasal absorbents, transpulmonary absorbents, percutaneous absorbents, and topical sustained-release agents. Liquid preparations can be prepared in accordance with known techniques. For example, a vaccine component is dissolved in an aseptic aqueous solution that is generally used for injection preparations, emulsified, and embedded in liposome. Peptide is likely to be degraded by peptidase or the like in vivo, and it has a problem in the accessibility to the target site. Thus, utilization of an adequate delivery method involving the use of liposome is a preferable embodiment of usage. The aforementioned method involving the use of liposome is an example of utilization of a peptide delivery technique, although such delivery technique is not limited thereto. Solid preparations can be prepared in accordance with known techniques. For example, an excipient, such as mannitol, trehalose, sorbitol, lactose, or glucose, is added to the vaccine component, and the resultant is lyophilized in that state. Further, such lyophilized preparations can be prepared in the form of powder preparations. Also, such powder can be mixed with polylactic acid, glycolic acid, or the like and prepared in the form of solid preparations. Gelled agents can be prepared in accordance with known techniques. For example, a vaccine component is dissolved in a thickener or polysaccharide, such as glycerine, polyethylene glycol, methylcellulose, carboxymethyl cellulose, hyaluronic acid, or chondroitin sulfate.

As stabilizers, human serum albumin, human immunoglobulin, $\alpha_2$-macroglobulin, amino acid, or the like can be added to any of such preparations. As dispersants or absorption promoters, also, alcohol, sugar alcohol, ionic surfactant, nonionic surfactant, or the like can be added, so as not to ruin activity of the vaccine component. Further, trace metals or organic acid salts can be optionally added.

A dose of a mimic peptide as the immunogen of the pharmaceutical composition of the present invention varies depending on activity of such peptide, the age and the body weight of the patient, a type or severity of the disease, and other conditions. In general, such dose for oral administration is 0.001 to 1,000 mg/kg of body weight per day, and it is 0.001 to 1,000 mg/kg of body weight per day in the case of hypodermic, intracutaneous, or nasal administration. In general, the number of times of administration is 1 to 3 times in the case of oral administration, and it is 1 or 2 times in the case of hypodermic, intracutaneous, or nasal administration.

BRIEF DESCRIPTION OF THE DRAWINGS

FIG. 5 shows a list of peptide sequences (SEQ ID NOS: 9-10, 33, 11-15, 34, 16, 16-20, 16 21-22, respectively) displayed on phage clones isolated with the use of B6 scFv, B7 scFv, or D1 scFv that inhibits Aβ1-42 fibrillogenesis as a template.

FIG. 6 (SEQ ID NOS: 9, 36, 23, 30, 24-27) shows fusion molecules of a biotinylated B6- or B7 scFv-binding sequence and a TAT sequence.

Figure 1:
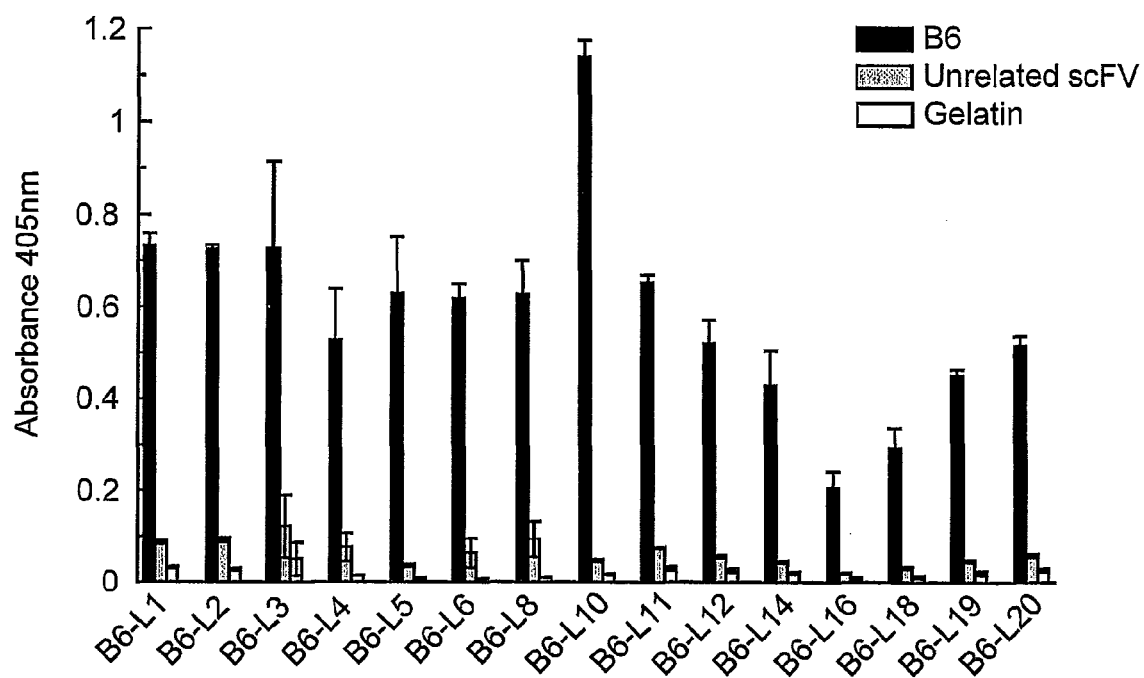
FIG. 1 shows the results of ELISA on peptide phage clones bound to B6 scFv.

This description includes part or all of the contents as disclosed in the description and/or drawings of Japanese Patent Application No. 2007-277638, which is a priority document of the present application.

BEST MODES FOR CARRYING OUT THE INVENTION

Hereafter, the present invention is described in greater detail with reference to production examples and examples, although the present invention is not limited thereto.

EXAMPLE 1

The following experiment was carried out in accordance with Kaji et al., J. Biochem. 129: 577-583, 2001 and S. Hashiguchi et al., J. Biochem. 133: 43-49, 2003.

1. Material and Method

(1) Purification of scFv Using E-Tag Column

In order to express scFv that binds to Aβ, *E. coli* HB2151 cells were infected with scFv phage clones by the method of Hashiguchi et al. (J. Biochem. 133: 43-49, 2003). Amyloid-specific scFvs (B6, B7, D1, and F10) were purified from the obtained medium supernatant using the E-tag column (Amersham Biosciences).

The amino acid sequence of the VH chain of B6scFv (clone B6 of WO 2005/105998) is represented by SEQ ID NO: 1 and the amino acid sequence of the VL chain of B6scFv is represented by SEQ ID NO: 2.

The amino acid sequence of the VH chain of B7scFv (clone B7 of WO 2005/105998) is represented by SEQ ID NO: 3 and the amino acid sequence of the VL chain of B7scFv is represented by SEQ ID NO: 4.

The amino acid sequence of the VH chain of D1 scFv (clone D1 of WO 2005/105998) is represented by SEQ ID NO: 5 and the amino acid sequence of the VL chain of D1 scFv is represented by SEQ ID NO: 6.

The amino acid sequence of the VH chain of F10scFv (clone F10 of WO 2005/105998) is represented by SEQ ID NO: 7 and the amino acid sequence of the VL chain of F10scFv is represented by SEQ ID NO: 8.

(2) Peptide Phage Library

The Ph.D.-12 library (New England Biolabs, MA) displaying 12 random amino acid sequences at the amino terminus of the phage gene III protein and the Ph.D.-C7C library (New England Biolabs, MA) displaying a peptide containing 7 amino acid sequences flanked by a pair of cysteine residues at the amino terminus of the phage gene III protein were used.

(3) Biopanning

The Maxisorp plate was coated with the template human single-stranded antibody (scFv: B6, B7, D1, or F10) or control scFv in an amount of 1 μg/100 μl/well (0.1 M NaHCO$_3$, pH 8.6) at 4° C. for 6 hours. Each well was blocked with 0.5% gelatin for the 1st panning, with 0.25% BSA for the 2nd panning, and with 0.5% gelatin for the 3rd panning at 4° C. for 14 hours. The 12-mer or C7C peptide phage library was diluted (1.5×10$^{12}$ pfu/100 μl) with a blocking solution and then allowed to stand for 30 minutes. Thereafter, absorption operation was performed using control scFv. Specifically, the well coated with control scFv was washed three times with 0.2% Tween 20/PBS (PBST), a phage solution was added thereto, and the reaction was allowed to proceed at room temperature for 1 hour. A phage solution that was not bound to control scFv was recovered. The phage solution was added to the well coated with scFv as a template, and the reaction was allowed to proceed at room temperature for 1 hour. Each well was washed 10 times with 0.2% PBST, 100 μl of 1 mg/ml BSA/0.1 M glycine hydrochloride (pH 2.2) was added thereto, the mixture was allowed to stand at room temperature for 5 minutes, the bound phages were recovered, and 15 μl of 1 M Tris-HCl (pH 9.1) was added thereto immediately thereafter to neutralize the phages. *E. coli* ER2738 was infected with the recovered phages for amplification. The amplified phages were used in the 2nd and 3rd rounds of panning (1.5×10$^{12}$ pfu/100 μl).

(4) Isolation of Phage Clones

After two rounds of panning, ER2738 was infected with the recovered phages and cultured on the LB/Tet/X-gal plate. ER2738 was infected again with the plaques resulting from lysis, and phage clones were isolated.

(5) ELISA

An ELISA plate was coated with scFv used as a template in the panning or with control scFv in an amount of 50 ng/40 μl/well (0.1 M NaHCO$_3$, pH 8.6) at 4° C. for 6 hours. Each well was blocked with 0.5% gelatin at 4° C. for 13 hours. Each well was washed three times with 0.2% PBST, the isolated peptide phage clone solution (approximately 1.6×10$^{11}$ virions/40 μl) was added, and the reaction was allowed to proceed at room temperature for 1 hour. After reaction with 40 μl of biotinylated anti-M13 monoclonal antibodies (diluted 1000-fold) and a streptavidin-alkaline phosphatase conjugate (diluted 1000-fold), the bound phages were detected using substrate p-nitrophenyl phosphate.

(6) Analysis of DNA Nucleotide Sequence

Phage clones that were confirmed to have specificity were treated with phenol/chloroform for protein removal. Thereafter, DNA was purified via ethanol precipitation and used as a template for nucleotide sequencing. A gene in the region having the random peptide sequence inserted therein was amplified using a primer-96g III (1 pg/μl): 5'-CCC TCA TAG TTA GCG TAA CG-3' (SEQ ID NO: 31)(New England Biolabs, MA) and subjected to DNA nucleotide sequencing.

(7) Peptide Synthesis

Peptides were synthesized according to a general solid-phase peptide synthesis method, i.e., the Fmoc/fBTu+HOBt method. A TAT sequence was ligated to each of the peptides B6-L1, B7-C15, and B7-S15 to synthesize peptides. For the peptide B7-C15, glycine was added to the carboxyl terminus, and a TAT sequence was then ligated thereto. In this context, a TAT sequence is a peptide sequence having the function of passing through the blood-brain barrier (P. Jarver and Ulo Langel, The use of cell-penetrating peptides as a tool for gene regulation, DDT, 9: 395-401, 2004).

The B6-L1, B7-C15, and B7-S15 sequences each having a TAT sequence fused at the amino terminus are referred to as TAT-B6-L1, TAT-B7-C15, and TAT-B7-S15, respectively. The B6-L1 sequence having a TAT sequence fused at the carboxyl terminus is referred to as B6-L1-TAT. In order to detect such peptide binding, peptide sequences comprising biotin bound to the amino terminuses were synthesized.

The amino acid sequences of B6-L1, B7-C15, and B7-S15 and fusion molecules thereof with a TAT sequence are represented by the following SEQ ID NOs:
B6-L1: SEQ ID NO: 9;
B7-C15: SEQ ID NO: 16
B7-S15: SEQ ID NO: 23
TAT-B6-L1: SEQ ID NO: 24
B6-L1-TAT: SEQ ID NO: 25
TAT-B7-C15: SEQ ID NO: 26
TAT-B7-S15: SEQ ID NO: 27

(8) Experiment of Inhibition of Amyloid β Fibrillogenesis

The synthesized peptide (TAT-B6-L1, B6-L1-TAT, TAT-B7-C15, or TAT-B7-S15) was added at various concentrations (1.65 nM, 16.5 nM, and 33 nM) to the Aβ1-42 peptide diluted to 40 μM using 20 mM phosphate buffer (pH 7.0). The sample (10 μl) was recovered 0, 6, and 24 hours thereafter, 90 μl of 11 μM thioflavine T (Sigma)/phosphate buffer was added, and fluorescence intensity at 482 nm generated by the excitation light at 450 nm was measured using a multilabel plate counter, Wallac 1420 ARVO sx (Perkin-Elmer; Wellesley, Mass.).

(9) Experiment of Precipitation of Aβ Conformers (Aβ Oligomers and Aβ Fibers) by Aβ Fibrillogenesis-Inhibiting Peptide Aβ1-42 was dissolved at a concentration of 40 μM in 20 mM phosphate buffer (pH 7.0). The TAT-B6-L1 or TAT-B7-C15 peptide adjusted to 40 μM was added 1.5 hours thereafter at a ratio of 1:1 by liquid volume, and the reaction was allowed to proceed at 37° C. for 1 hour (final concentration: Aβ (20 μM)/synthesized peptide (20 μM)). After the reaction, an aliquot thereof was sampled as a sample before immunoprecipitation ("Before precipitation"), and the remaining sample was reacted with M-280 streptavidin-magnet beads (Dynal Biotech, Oslo, Norway) adjusted to 20 μg/μl on ice for 1 hour at a ratio of 1:1 by liquid volume (final concentration: Aβ (10 μM)/synthesized peptide (10 μM)/beads (10 μg/μl)). After the reaction, the beads were precipitated using a magnet to obtain "Supernatant." To the precipitated beads, PBS was added in a liquid volume equal to that of the recovered supernatant to obtain a "Precipitate." Each obtained sample was electrophoresed and subjected to Western blot analysis using anti-Aβ antibodies.

2. Results (1) Peptide Phage Clones that Bind to Aβ-Specific scFv (a) Results of ELISA conducted on peptide phage clones bound to B6 scFv are shown in FIG. 1. Fv1E1, an antibody that does not inhibit Aβ fibrillogenesis, was used as unrelated scFv (control scFv). The Ph.D.-12 library (New England Biolabs, MA) displaying a 12-mer amino acid sequence was used. The experiment was conducted according to the procedures described in the above "(5) ELISA".

Figure 2:
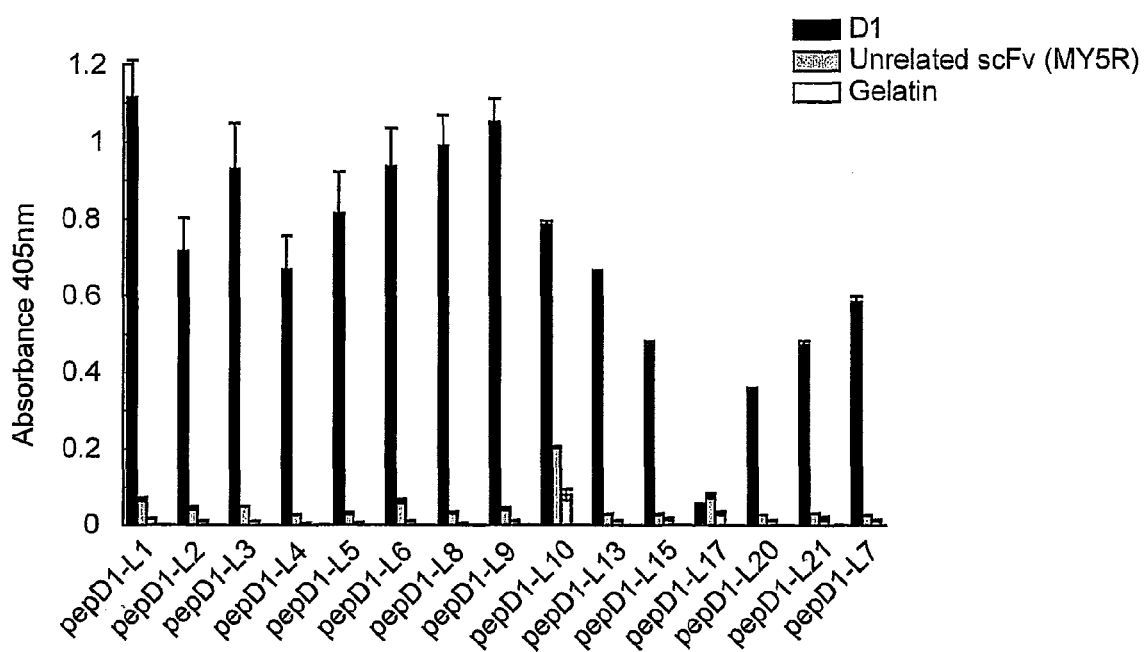
FIG. 2 shows the results of ELISA on 12-mer peptide phage clones bound to D1 scFv.

(b) Results of ELISA conducted on 12-mer peptide phage clones bound to D1 scFv are shown in FIG. 2. MY5R, an antibody that does not inhibit Aβ fibrillogenesis, was used as unrelated scFv (control scFv). The Ph.D.-12 library (New England Biolabs, MA) displaying a 12-mer amino acid sequence was used. The experiment was conducted according to the procedures described in the above "(5) ELISA".

Figure 3:
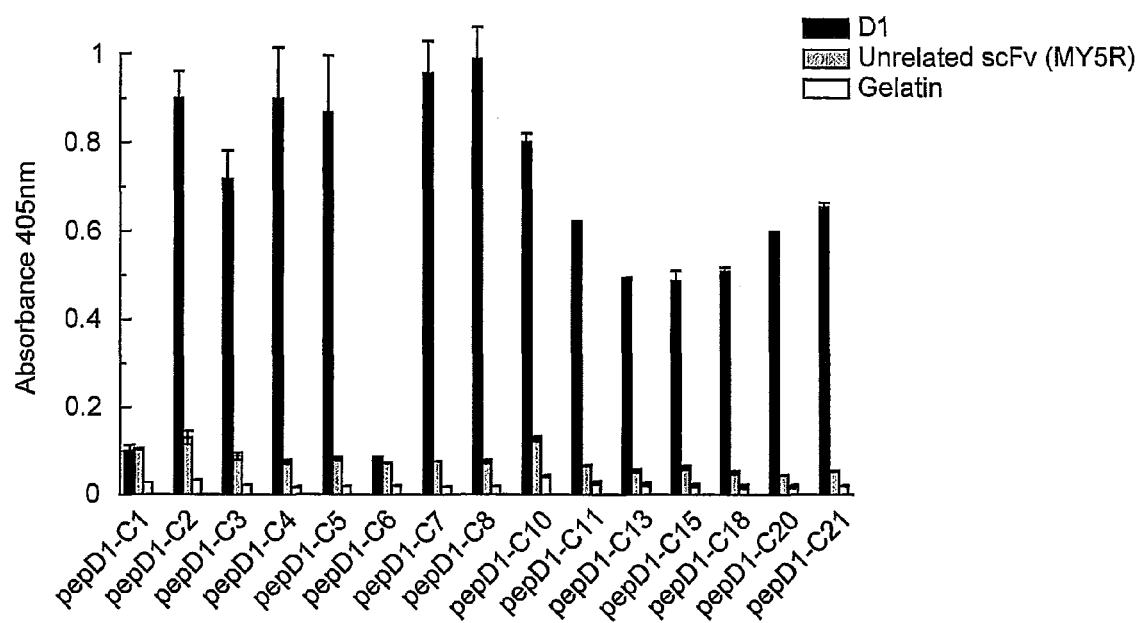
FIG. 3 shows the results of ELISA on C7C peptide phage clones bound to D1 scFv.

(c) Results of ELISA conducted on C7C peptide phage clones bound to D1 scFv are shown in FIG. 3. MY5R, an antibody that does not inhibit Aβ fibrillogenesis, was used as unrelated scFv (control scFv). The Ph.D.-C7C library (New England Biolabs, MA) displaying a peptide containing 7 amino acid sequences flanked by a pair of cysteine residues was used. The experiment was conducted according to the procedures described in the above "(5) ELISA".

(2) Activity of Inhibiting Aβ1-42 Fibrillogenesis by B6-Binding Peptide Phages

Figure 4:
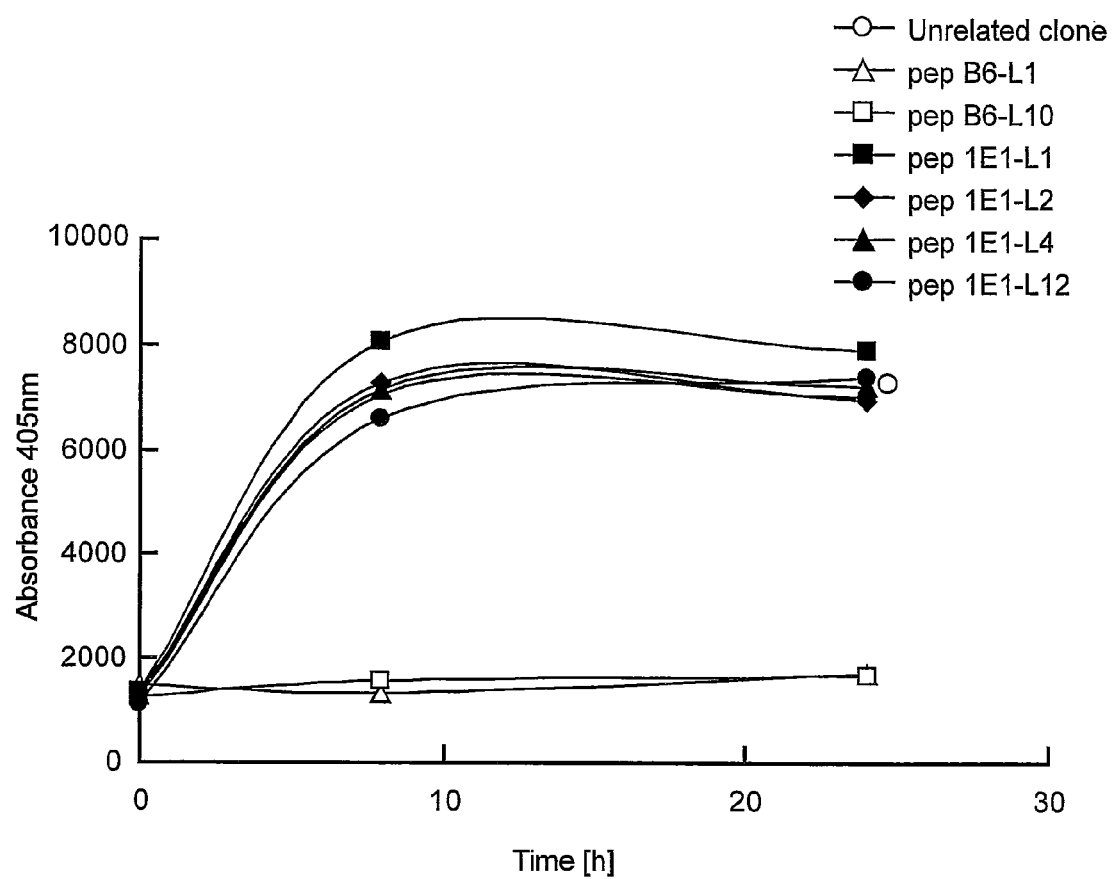
FIG. 4 shows the results of an experiment of inhibition of Aβ1-42 peptide fibrillogenesis by peptide phages.

Results of an experiment of inhibition of Aβ1-42 peptide fibrillogenesis by B6-binding peptide phages are shown in FIG. 4. The experiment of inhibition of Aβ1-42 fibrillogenesis was conducted according to the procedures described in the above "(8) Experiment of inhibition of amyloid β fibrillogenesis". pepB6-L1 and pepB6-L10 are phage clones isolated using, as a template, B6 scFv that inhibits Aβ1-42 fibrillogenesis, and these phage clones bind thereto. pep1E1-L1, pep1E1-L2, pep1E1-L4, and pep1E1-L12 are phage clones isolated using, as a template, Fv1E1 scFv (described in the paragraphs [0074] to [0075] in WO 2005-105998) that does not inhibit Aβ1-42 fibrillogenesis. The concentrations of the phage clones used herein are $3.0 \times 10^{12}$ virions/ml.

(3) Aβ-Specific scFv Epitope (Binding Sequence)

A list of amino acid sequences of peptides displayed on phage clones isolated using, as a template, B6 scFv, B7 scFv, or D1 scFv that inhibits Aβ1-42 fibrillogenesis is shown in FIG. 5. The Ph.D.-12 library (abbreviated as "12mer*" in FIG. 5) or the Ph.D.-7C library (abbreviated as "C7C*" in FIG. 5) were used as phage libraries. pepB7-C15, pepB6-C2, C5, C6, C7, C8, C9, C10, and C15, and pepD1-05, C7, and C20 had the same sequence. L and C indicated before the number represent clones isolated from the 12-mer and C7C libraries, respectively.

The amino acid sequence of a peptide displayed on each phage clone is represented by the following SEQ ID NOs:
pepB6-L1: SEQ ID NO: 9;
pepB6-L10: SEQ ID NO: 10;
pepD1-L5, L9: SEQ ID NO: 11;
pepD1-L6: SEQ ID NO: 12;
pepD1-L7: SEQ ID NO: 13;
pepD1-L13: SEQ ID NO: 14;
pepD1-L20: SEQ ID NO: 15;
pepB7-C15 (pepB6-C2, C5, C6, C7, C8, C9, C10, and C15 and pepD1-C5, C7, and C20): SEQ ID NO: 16;
pepD1-C2, C13: SEQ ID NO: 17;
pepD1-C18: SEQ ID NO: 18;
pepD1-C3: SEQ ID NO: 19;
pepD1-C11: SEQ ID NO: 20;
pepD1-C8: SEQ ID NO: 21;
pepD1-C10: SEQ ID NO: 22

(4) Fusion Molecule of Biotinylated B6 or B7 scFv-Binding Sequence and TAT Sequence A fusion molecule of a biotinylated B6 scFv-binding sequence and a TAT sequence is shown in FIG. 6. The B6-L1, B7-C15, and B7-S15 sequences each having a TAT sequence fused at the amino terminus are referred to as TAT-B6-L1, TAT-B7-C15, and TAT-B7-S15, respectively. The B6-L1 sequence having a TAT sequence fused at the carboxyl terminus is referred to as B6-L1-TAT. A TAT sequence is a peptide sequence having the function of passing through the blood-brain barrier (P. Jarver and Ulo Langel, The use of cell-penetrating peptides as a tool for gene regulation, DDT, 9: 395-402, 2004). These peptides were biotinylated at the amino terminuses, and such peptides binding was quantified using avidin labeled with an enzyme.

Figure 7:
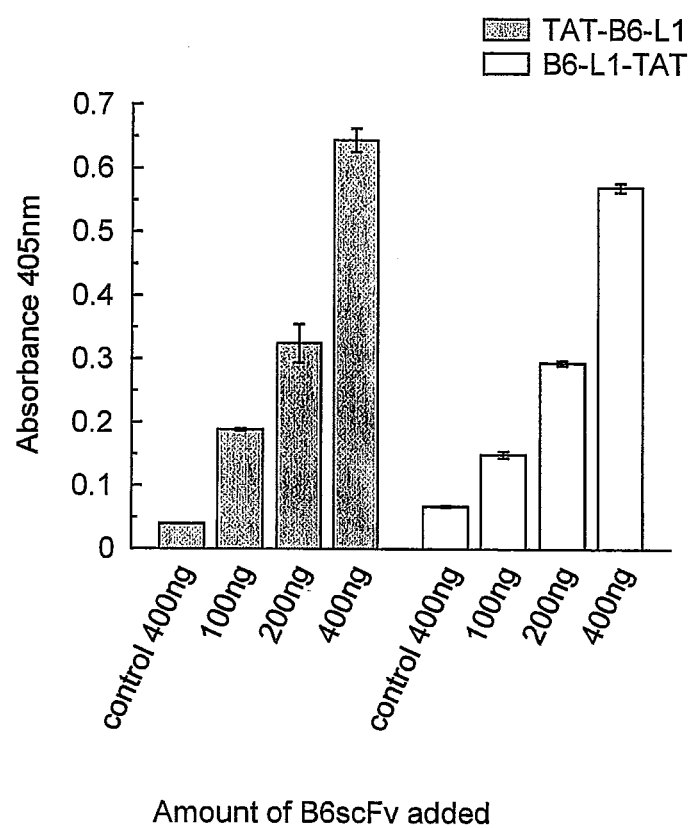
FIG. 7 shows that a fusion peptide of TAT and B6-L1 is recognized by B6 scFv.

(5) The fusion peptide of TAT and B6-L1 was recognized by B6 scFv (FIG. 7). An ELISA plate was coated with the synthesized peptide TAT-B6-L1 or B6-L1-TAT under conditions of 200 ng/well. After addition of B6 scFv at various concentrations, binding activity thereof was inspected. A control peptide used was an unrelated peptide (GSGGGSCGY-WRSEWGLCG)(SEQ ID NO: 32). Binding reaction dependent on the amount of B6 scFv was observed.

Figure 8:
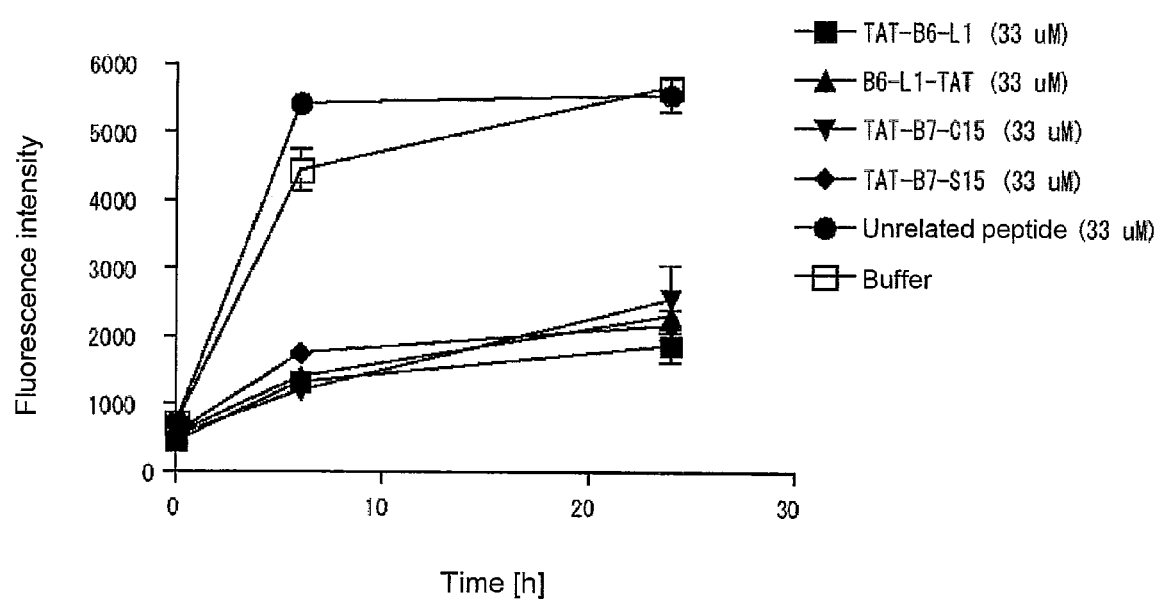
FIG. 8 shows the results of measuring activity of inhibiting Aβ1-42 fibrillogenesis by a fusion peptide of TAT and B6-L1, B7-C15, or B7-S15.

Results of measuring activity of inhibiting Aβ1-42 fibrillogenesis by a fusion peptide of TAT and B6-L1, B7-C15, or B7-S15 are shown in FIG. 8. The experiment of inhibition of fibrillogenesis was conducted according to the procedures described in the experiment of inhibition of fibrillogenesis above. TAT-B6-L1, B6-L1-TAT, TAT-B7-C15, and TAT-B7-S15 were demonstrated to have the activity of inhibiting fibrillogenesis. The control peptide exhibited no inhibiting activity.

Figure 9:
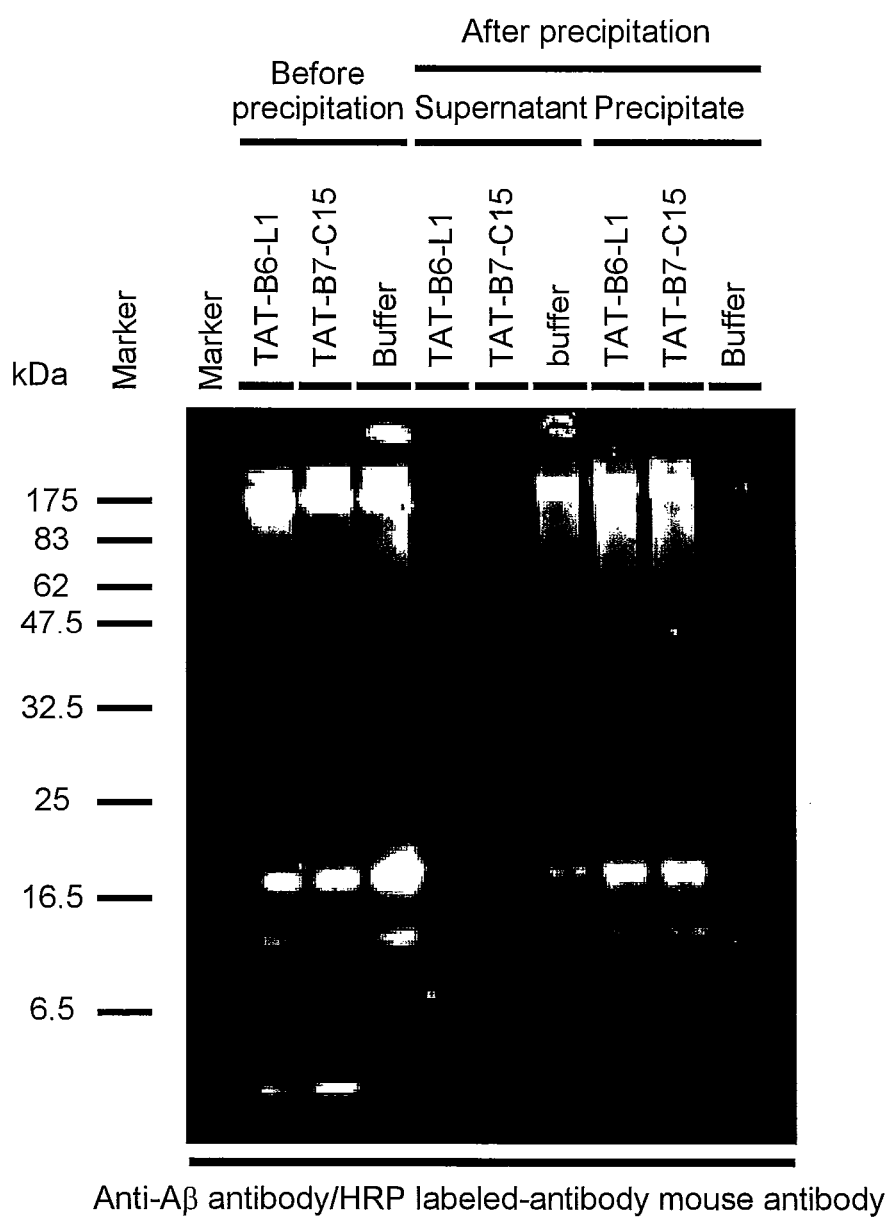
FIG. 9 shows the results of an experiment of precipitation of Aβ conformers (Aβ oligomers and Aβ fibers) by a fusion peptide of TAT and B6-L1 or B7-C15.

(7) Experiment of Precipitation of Aβ Conformers (Aβ Oligomers and Aβ Fibers) by TAT-B6-L1 or TAT-B7-C15 Peptide Results of an experiment of precipitation of the TAT-B6-L1 or TAT-B7-C15 peptide are shown in FIG. 9. Aβ1-42 was dissolved at a concentration of 40 μM in 20 mM phosphate buffer (pH 7.0). The biotinylated TAT-B6-L1 or TAT-B7-C15 peptide was added thereto 1.5 hours thereafter, and the conjugates were precipitated using streptavidin-magnet beads. Although bands derived from Aβ oligomers, Aβ fibers, etc., were observed before precipitation, Aβ oligomers or Aβ fibers were not observed in the supernatant resulting from precipitation using the TAT-B6-L1 or TAT-B7-C15 peptide, and such Aβ oligomers or Aβ fibers were observed in the precipitate. These results demonstrate that Aβ oligomers or Aβ fibers formed 1.5 hours after the dissolution of Aβ1-42 bind to the TAT-B6-L1 or TAT-B7-C15 peptide. No precipitation reaction was observed in the unrelated control peptide (not shown in FIG. 9).

EXAMPLE 2

1. Material and Method (1) Preparation of Antigen and Immunization

Streptavidin (6.6 μM) adjusted at given concentrations with PBS was mixed with biotinylated TAT-B7-C15, TAT-B7-S15, or TAT-B6-L1 peptide (26.4 μM) obtained in "Peptide synthesis" in Example 11. (7) at a ratio of 1:1 by volume (total protein concentration: 500 μg/ml), and the reaction was allowed to proceed at 4° C. overnight to prepare a streptavidin conjugate (SA-Ag). Aluminum hydroxide gel (20 mg/ml) as an adjuvant was mixed with SA-Ag (500 μg/ml) at a ratio of 1:1 by volume with agitation to adsorb SA-Ag to the aluminum hydroxide gel. A 8-week-old female BALB/c mouse was immunized hypodermically with 200 μl of an aluminum hydroxide gel/SA-Ag suspension (aluminum hydroxide gel: 2 mg; SA-Ag: 50 μg). The first immunization was designated as that of "day 0," and the mouse was immunized on days 15, 30, 60, and 90 (5 times in total) in the same manner as above. Fibrotic Aβ was mixed with aluminum hydroxide gel, and the mouse immunized therewith was designated as a positive control. PBS was added to aluminum hydroxide gel, and the mouse immunized therewith was designated as a negative control.

(2) Sampling of Blood Serum

Blood was collected from the eyeground of the mouse on days 14, 29, 59, 74, and 100, the collected blood was mixed with an equivalent amount of PBS, and the mixture was centrifuged at 6,000 rpm for 10 minutes, in order to sample the blood serum component (diluted 2-fold).

(3) Detection of Anti-Aβ Antibody in Blood Serum

Fibrotic Aβ1-42 and soluble Aβ1-42 were added to a 96-well plastic plate, and the plate was coated at 4° C. overnight (50 ng/40 μl/well). The wells were blocked with 0.5% gelatin for 2 hours and washed with 0.1% Tween 20/PBS. Thereafter, the blood serum of day 74, which had been diluted 200-fold with PBS (relative to undiluted blood serum), was added, and the reaction was allowed to proceed at room temperature for 1 hour. After the wells were washed three times with 0.1% Tween 20/PBS, the alkaline phosphatase-labeled anti-mouse IgG+IgM antibody diluted 5.000-fold was added, and the reaction was allowed to proceed at room temperature for 1 hour. After the plate was washed three times with 0.1% Tween 20/PBS, a substrate solution containing p-nitrophenyl phosphate (2 mg/ml) was added, and the absorbance at 405 nm was assayed using a microplate reader. The results are obtained by subtracting the values representing the reaction of the blood sera with the backgrounds; i.e., 0.5% gelatin.

The non-specific binding activity (absorbance at 405 nm; the subtracted OD value) of the blood sera (experimental groups) to 0.5% gelatin is shown below.

Fibrotic Aβ(Aβ): 0.07; TAT-B7-C15: 0.035; TAT-B6-L1: 0.0255; TAT-B7-S15: 0.058; PBS: 0.024; none: 0.0165

2. Results

Induction of an antibody that binds to fibrotic Aβ was observed in the mouse immunized with the Aβ mimic peptide. Since binding activity to soluble Aβ is at a background level; further, it was found that the Aβ mimic peptide would imitate the three-dimensional structure of fibrotic Aβ and would induce an antibody specific for fibrotic Aβ. Such binding activity value was found to be equivalent to that of the mouse immunized with fibrotic Aβ as a positive control. The results are shown in FIG. 10.

Figure 10:
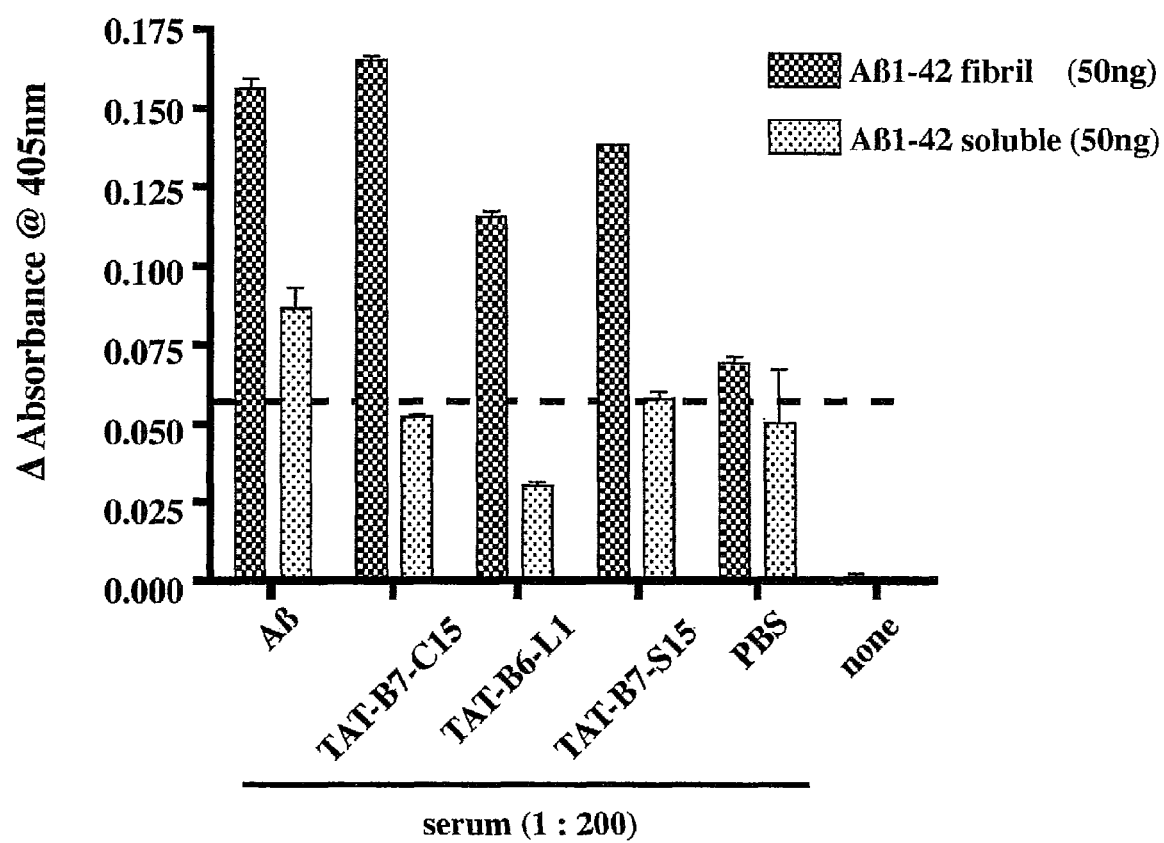
FIG. 10 shows the results of an experiment of induction of an anti-Aβ antibody in a mouse immunized with a Aβ mimic peptide.

In FIG. 10, the x axis represents a molecule that had immunized the mouse, and the y axis represents intensity of the antibody reaction (i.e., absorbance at 405 nm). The term "Aβ-42 soluble" represents the amount of an antibody reacting with soluble Aβ (normal Aβ) and the term "Aβ1-42 fibril" represents the amount of an antibody reacting with abnormal fibrotic Aβ. The broken line represents the activity value of non-specific binding of the blood serum component immunized with aluminum hydroxide gel/PBS to Aβ as an indicator of the background.

If a mouse is immunized with fibrotic Aβ, it reacts with soluble Aβ to some extent, and an antibody that strongly reacts with fibrotic Aβ is produced (Aβ on axis x of FIG. 10). When immunized with other mimic peptides, the amount of the detected antibody reacting with soluble Aβ is half or less than that of a non-specific antibody produced via administration of phosphate buffer (PBS) alone. This indicates that an antibody reacting with fibrotic Aβ significantly induces an antibody at substantially the same level as that attained when real fibrotic Aβ is immunized.

Abnormal amyloid β exhibits toxicity in nerve cells in the brain and induces apoptosis. Thus, the predominant symptoms of Alzheimer's disease (i.e., dementia) are developed.

The antibody induced by the mimic peptide of the present invention does not react with a normal amyloid molecule. Thus, the immune response to the normal self-component does not occur, and side effects do not occur. Such antibody, however, binds to an abnormal amyloid β peptide aggregate (amyloid β fibers, oligomers, or globulomers). As a result, pathogenic abnormal amyloid molecules are withdrawn from the brain into the blood, they are phagocytized by phagocytic microglia cells in the brain, and abnormal amyloid β in the brain is removed. Accordingly, an antibody specific for the abnormal amyloid β molecules induced by the vaccine of interest eliminates the killer molecules from the brain. Thus, prevention and treatment of Alzheimer's disease can be realized.

All publications, patents, and patent applications cited herein are incorporated herein by reference in their entirety Industrial Applicability The present invention provides a vaccine or immunogen that induces production of an antibody specific for an abnormal amyloid β peptide.

The invention claimed is:

1. An immunogen comprising
a peptide consisting of 8 to 30 amino acid residues, wherein the peptide comprises
the amino acid sequence of Tyr-Gly-Thr-Lys-Pro-Trp-Met (SEQ ID NO: 28),
the amino acid sequence of Leu-Asp-Ile-Phe-Ala-Pro-Ile (SEQ ID NO: 29), or a
conjugate of SEQ ID NO: 28 and/or SEQ ID NO: 29; and
a pharmaceutically acceptable carrier.

2. The immunogen according to claim 1, which contains a peptide consisting of 9 to 30 amino acid residues, wherein the peptide comprises
the amino acid sequence of,

```
                              (SEQ ID NO: 35)
Cys-Tyr-Gly-Thr-Lys-Pro-Trp-Met-Cys
(Ia)
``` the amino acid sequence of Ser-Tyr-Gly-Thr-Lys-Pro-Trp-Met-Ser-Gly (SEQ ID NO: 23),
the amino acid sequence of Gly-Met-Leu-Asp-Ile-Phe-Ala-Pro-Ile-Arg-His-Val (SEQ ID NO: 9), or a conjugate of any of the amino acid sequences of SEQ ID NOs: 9, 23, and/or 35; and,
a pharmaceutically acceptable carrier, wherein the two cysteine residues of SEQ ID NO: 35 are optionally crosslinked.

3. The immunogen according to claim 1, wherein the peptide consists of 20 to 30 amino acid residues containing the aforementioned amino acid sequence or sequences and a TAT sequence represented by formula:

```
                              (SEQ ID NO: 30)
Tyr-Gly-Arg-Lys-Lys-Arg-Arg-Gln-Arg-Arg-Arg.
```

4. A method for inhibiting amyloid β fibrillogenesis comprising administering an effective amount of the immunogen according to any one of claims 1-3 to a subject in need thereof.

5. A method for inducing production of an antibody specific for abnormal amyloid β peptide comprising administering an effective amount of the immunogen according to any one of claims 1-3 to a subject in need thereof.

* * * * *

SEQUENCE LISTING

<160> NUMBER OF SEQ ID NOS: 36

<210> SEQ ID NO 1
<211> LENGTH: 123
<212> TYPE: PRT
<213> ORGANISM: Homo sapiens

<400> SEQUENCE: 1

```
Gln Val Gln Leu Val Gln Ser Gly Gly Gly Val Val Gln Pro Gly
  1               5                  10                 15

Ser Leu Arg Leu Ser Cys Ala Ala Ser Gly Phe Thr Phe Ser Arg Tyr
             20                  25                  30

Ala Met Ser Trp Val Arg Gln Ala Pro Gly Lys Gly Leu Glu Trp Val
         35                  40                  45

Ser Ala Met Ser Gly Ser Gly Asp Thr Thr Tyr Tyr Ala Asp Ser Val
 50                  55                  60

Lys Gly Arg Phe Thr Ile Ser Arg Asp Asn Ser Lys Thr Val Tyr
 65                  70                  75                  80

Leu Gln Met Asn Arg Leu Arg Val Glu Asp Thr Ala Ile Tyr Tyr Cys
             85                  90                  95

Ala Lys Asp Gly Arg Phe Arg Asn Arg Arg Ser Asp Gly Phe Asp Thr
            100                 105                 110

Trp Gly Gln Gly Thr Leu Val Thr Val Ser Ser
            115                 120
```

```
<210> SEQ ID NO 2
<211> LENGTH: 109
<212> TYPE: PRT
<213> ORGANISM: Homo sapiens

<400> SEQUENCE: 2
```

```
Ser Ser Glu Leu Thr Gln Asp Pro Ala Val Ser Val Ala Leu Gly Gln
  1               5                  10                 15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asp Asn Arg Pro Ser Gly Ile Pro Asp Arg Phe Ser Gly Ser
 50                  55                  60

Ser Ser Gly Asn Ala Ala Ser Leu Thr Ile Thr Gly Ala Gln Ala Glu
 65                  70                  75                  80

Asp Glu Ala Asp Tyr Tyr Cys Asn Ser Arg Asp Thr Ser Gly Asn His
             85                  90                  95

Leu Val Phe Gly Gly Gly Thr Lys Val Thr Val Leu Gly
            100                 105
```

```
<210> SEQ ID NO 3
<211> LENGTH: 123
<212> TYPE: PRT
<213> ORGANISM: Homo sapiens

<400> SEQUENCE: 3
```

```
Gln Val Gln Leu Val Gln Ser Gly Gly Gly Leu Val Gln Pro Gly Gly
  1               5                  10                 15

Ser Gln Arg Leu Ser Cys Ala Ala Ser Gly Phe Gly Phe Ser Asn Tyr
             20                  25                  30

Ala Val Ser Trp Val Arg Gln Ala Pro Gly Thr Gly Leu Glu Trp Val
         35                  40                  45

Ala Gly Val Asn Gly Gly Gly Gln Asn Thr Phe Tyr Ala Asp Ser Val
 50                  55                  60

Lys Gly Arg Phe Thr Ile Ser Arg Asp Asn Ser Lys Thr Val Tyr
 65                  70                  75                  80

Leu Gln Met Asn Ser Leu Arg Val Glu Asp Thr Ala Ile Tyr Tyr Cys
             85                  90                  95

Ala Lys Asp Gly Arg Phe Arg Asn Arg Arg Pro Asp Gly Phe Asp Thr
```

```
                    100                 105                 110
Trp Gly Gln Gly Thr Leu Val Thr Val Ser Ser
            115                 120

<210> SEQ ID NO 4
<211> LENGTH: 109
<212> TYPE: PRT
<213> ORGANISM: Homo sapiens

<400> SEQUENCE: 4

Ser Ser Glu Leu Thr Gln Asp Pro Asn Val Ser Val Ala Leu Gly Gln
1               5                   10                  15

Thr Val Arg Ile Thr Cys Gln Gly Asp Thr Leu Arg Asn Asn Phe Pro
            20                  25                  30

Thr Trp Tyr Gln Gln Lys Pro Gly Gln Ala Pro Val Leu Val Phe Tyr
        35                  40                  45

Gly Lys Asp Asn Arg Pro Ser Gly Ile Pro Asp Arg Phe Ser Gly Ser
50                  55                  60

Arg Ser Gly Thr Thr Ala Ser Leu Val Ile Thr Gly Ala Gln Ala Gln
65                  70                  75                  80

Asp Glu Ala Asp Tyr Tyr Cys Asn Ser Arg Asp Ser Gly Gly His His
                85                  90                  95

Leu Val Phe Gly Gly Gly Thr Lys Leu Thr Val Leu Gly
            100                 105

<210> SEQ ID NO 5
<211> LENGTH: 117
<212> TYPE: PRT
<213> ORGANISM: Homo sapiens

<400> SEQUENCE: 5

Gln Val Thr Leu Lys Glu Ser Gly Gly Asp Leu Val Lys Pro Gly Gly
1               5                   10                  15

Ser Leu Arg Leu Ser Cys Ala Ala Ser Gly Phe Thr Phe Arg Lys Tyr
            20                  25                  30

Tyr Met Ala Trp Ile Arg Gln Ala Pro Gly Lys Gly Pro Glu Trp Leu
        35                  40                  45

Ser Thr Ile Ser Asn Ser Gly Asp Ile Ile Tyr Ala Asp Ser Val
50                  55                  60

Arg Gly Arg Phe Ser Ile Ser Arg Asp Asn Ala Gln Lys Ser Leu Tyr
65                  70                  75                  80

Leu Gln Met Thr Ser Leu Arg Pro Asp Asp Ser Ala Ile Tyr Tyr Cys
                85                  90                  95

Ala Arg Glu Tyr Phe Phe Ser Phe Asp Val Trp Gly Arg Gly Thr Leu
            100                 105                 110

Val Thr Val Ser Ser
        115

<210> SEQ ID NO 6
<211> LENGTH: 109
<212> TYPE: PRT
<213> ORGANISM: Homo sapiens

<400> SEQUENCE: 6

Ser Ser Glu Leu Thr Gln Asp Pro Ala Val Ser Val Ala Leu Gly Gln
1               5                   10                  15

Thr Ile Arg Ile Thr Cys Gln Gly Asp Ser Leu Arg Ser Tyr Tyr Ala
            20                  25                  30
```

-continued

```
Ser Trp Tyr Gln Gln Lys Pro Gly Gln Ala Pro Val Leu Val Ile Tyr
            35                  40                  45

Gly Lys Asn Lys Arg Pro Ser Gly Ile Pro Asp Arg Ile Ser Gly Ser
 50                  55                  60

Arg Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Leu Val Phe Gly Gly Gly Thr Gln Leu Thr Val Leu Gly
            100                 105

<210> SEQ ID NO 7
<211> LENGTH: 125
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Arg Ile Ile Pro Ile Leu Gly Ile Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Lys Arg Phe Ala Ala Ala Arg Arg Gly Leu Asp Ala Phe
            100                 105                 110

Asp Ile Trp Gly Gln Gly Thr Met Val Thr Val Ser Ser
        115                 120                 125

<210> SEQ ID NO 8
<211> LENGTH: 109
<212> TYPE: PRT
<213> ORGANISM: Homo sapiens

<400> SEQUENCE: 8

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Leu Val Phe Gly Gly Gly Thr Lys Leu Thr Val Leu Gly
            100                 105

<210> SEQ ID NO 9
<211> LENGTH: 12
<212> TYPE: PRT
```

```
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 9

Gly Met Leu Asp Ile Phe Ala Pro Ile Arg His Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 10

Thr Ser Pro Ile Leu Asp Val Leu Thr Pro Pro Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 11

Gly Ser Pro Phe Leu Asp Leu Leu Ala Pro Ala Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 12

Ser Ser Ile Ile Asp Ile Leu Leu Pro Pro Ile Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 13

Ser Ile Leu Asp Ile Leu Ser Pro Arg Leu Ala Glu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 14

Gly Asn Thr Leu Leu Asp Thr Leu Val Pro Leu Ile
1               5                   10
```

```
<210> SEQ ID NO 15
<211> LENGTH: 12
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 15

Asn Pro Leu Asp Phe Tyr Ala Pro Ser Ile Leu Pro
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 16

Cys Tyr Gly Thr Lys Pro Trp Met Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 17

Cys Tyr Gly Thr Glu Pro Trp Met Cys
1               5

<210> SEQ ID NO 18
<211> LENGTH: 9
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 18

Cys Phe Gly His Glu Pro Trp Met Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 19

Cys Gln Gly His Leu Pro Trp Met Cys
1               5

<210> SEQ ID NO 20
<211> LENGTH: 9
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 20
```

Cys Phe Gly His Lys Pro Trp Met Cys
1               5

<210> SEQ ID NO 21
<211> LENGTH: 9
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 21

Cys Phe Gly Arg Leu Pro Trp Met Cys
1               5

<210> SEQ ID NO 22
<211> LENGTH: 9
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 22

Cys Phe Gly Ser Leu Pro Trp Met Cys
1               5

<210> SEQ ID NO 23
<211> LENGTH: 10
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 23

Ser Tyr Gly Thr Lys Pro Trp Met Ser Gly
1               5                   10

<210> SEQ ID NO 24
<211> LENGTH: 23
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 24

Tyr Gly Arg Lys Lys Arg Arg Gln Arg Arg Gly Met Leu Asp Ile
1               5                   10                  15

Phe Ala Pro Ile Arg His Val
            20

<210> SEQ ID NO 25
<211> LENGTH: 23
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 25

Gly Met Leu Asp Ile Phe Ala Pro Ile Arg His Val Tyr Gly Arg Lys
1               5                   10                  15

Lys Arg Arg Gln Arg Arg Arg
            20

```
<210> SEQ ID NO 26
<211> LENGTH: 21
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 26

Tyr Gly Arg Lys Lys Arg Arg Gln Arg Arg Cys Tyr Gly Thr Lys
1               5                   10                  15

Pro Trp Met Cys Gly
            20

<210> SEQ ID NO 27
<211> LENGTH: 21
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 27

Tyr Gly Arg Lys Lys Arg Arg Gln Arg Arg Ser Tyr Gly Thr Lys
1               5                   10                  15

Pro Trp Met Ser Gly
            20

<210> SEQ ID NO 28
<211> LENGTH: 7
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 28

Tyr Gly Thr Lys Pro Trp Met
1               5

<210> SEQ ID NO 29
<211> LENGTH: 7
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 29

Leu Asp Ile Phe Ala Pro Ile
1               5

<210> SEQ ID NO 30
<211> LENGTH: 11
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 30

Tyr Gly Arg Lys Lys Arg Arg Gln Arg Arg Arg
1               5                   10

<210> SEQ ID NO 31
<211> LENGTH: 20
<212> TYPE: DNA
```

```
<213> ORGANISM: Artificial Sequence
<220> FEATURE:
<223> OTHER INFORMATION: Synthetic primer

<400> SEQUENCE: 31
ccctcatagt tagcgtaacg                                                      20

<210> SEQ ID NO 32
<211> LENGTH: 18
<212> TYPE: PRT
<213> ORGANISM: Artificial Sequence
<220> FEATURE:
<223> OTHER INFORMATION: Designed peptide based on the sequence
      unrelated to B6 scFv

<400> SEQUENCE: 32

Gly Ser Gly Gly Gly Ser Cys Gly Tyr Trp Arg Ser Glu Trp Gly Leu
1               5                   10                  15

Cys Gly

<210> SEQ ID NO 33
<211> LENGTH: 12
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 33

Arg Val Asp Ile Leu Asn Tyr Leu Ser Pro Pro Ile
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 34

Ser Pro Leu Phe Ala Met Leu Ala Pro Ala Val Asp
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 35

Cys Tyr Gly Thr Lys Pro Trp Met Cys
1               5

<210> SEQ ID NO 36
<211> LENGTH: 10
<212> TYPE: PRT
<213> ORGANISM: Artificial Sequence
<220> FEATURE:
<223> OTHER INFORMATION: Designed peptide based on the DNA sequence of
      phage binding to human antiamyloid beta peptide antibody

<400> SEQUENCE: 36

Cys Tyr Gly Thr Lys Pro Trp Met Cys Gly
1               5                   10
```